United States Patent
Li et al.

(10) Patent No.: US 12,066,424 B1
(45) Date of Patent: Aug. 20, 2024

(54) DEEP ROCK IN SITU ENVIRONMENT RECONSTRUCTION AND INTEGRATED THREE-DIMENSIONAL MECHANICAL-THERMO-ACOUSTO-SEISMIC-FLOW TESTING METHOD

(71) Applicant: SHENZHEN UNIVERSITY, Shenzhen (CN)

(72) Inventors: Minghui Li, Shenzhen (CN); Heping Xie, Shenzhen (CN); Jun Lu, Shenzhen (CN); Mingzhong Gao, Shenzhen (CN); Cunbao Li, Shenzhen (CN); Hongwei Zhou, Shenzhen (CN); Cancan Chen, Shenzhen (CN); Zhouqian Wu, Shenzhen (CN); Delei Shang, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 0 days.

(21) Appl. No.: 18/588,083

(22) Filed: Feb. 27, 2024

(30) Foreign Application Priority Data

Mar. 2, 2023 (CN) .......................... 202310192077.2

(51) Int. Cl.
*G01N 33/24* (2006.01)
*G01N 29/04* (2006.01)
*G01N 29/22* (2006.01)
*G01N 29/44* (2006.01)

(52) U.S. Cl.
CPC ............ *G01N 33/24* (2013.01); *G01N 29/046* (2013.01); *G01N 29/223* (2013.01); *G01N 29/228* (2013.01); *G01N 29/4409* (2013.01)

(58) Field of Classification Search
CPC .... G01N 33/24; G01N 29/046; G01N 29/223; G01N 29/228; G01N 29/4409
USPC .......................................................... 73/863
See application file for complete search history.

(56) References Cited

FOREIGN PATENT DOCUMENTS

| CN | 102735548 A | * | 10/2012 | ......... G01N 15/0826 |
|----|-------------|---|---------|------------------------|
| CN | 102735548 B |   | 10/2012 |                        |
| CN | 102735549 A | * | 10/2012 |                        |
| CN | 102735600 A | * | 10/2012 |                        |
| CN | 104677815 A | * | 6/2015  |                        |

(Continued)

OTHER PUBLICATIONS

CN_102735600 Oct. 17, 2012 (Year: 2012).*

*Primary Examiner* — Octavia Hollington
*Assistant Examiner* — Monica S Young
(74) *Attorney, Agent, or Firm* — Jeenam Park

(57) ABSTRACT

The present invention relates to a deep rock in situ environment reconstruction and integrated three-dimensional mechanical-thermo-acousto-seismic-flow testing method, which comprises: preparing a cubic sample; placing the cubic sample in a sample holder; extending the 6 indenters to butt with the sample holder; butting 6 butting indenters with the 6 indenters; butting each of 6 hydraulic actuators with one of the butting indenters, performing stress loading on the cubic sample by the hydraulic actuator, filling a fluid medium into the cubic sample by a percolation medium channel, and dynamically measuring related parameters. The present application can achieve three-way multi-parameter synchronous monitoring and acquisition of deformation, acoustic emission, ultrasonic wave, temperature field, percolation field and heat flow field.

10 Claims, 17 Drawing Sheets

(56) References Cited

FOREIGN PATENT DOCUMENTS

| CN | 110132820 | A | * | 8/2019 | ......... G01N 15/0826 |
|---|---|---|---|---|---|
| CN | 111443026 | B | | 7/2020 | |
| CN | 114778311 | A | * | 7/2022 | ............. G01N 1/286 |
| CN | 115753417 | A | * | 3/2023 | |
| CN | 116087468 | A | * | 5/2023 | |

* cited by examiner

DEEP ROCK IN SITU ENVIRONMENT RECONSTRUCTION AND INTEGRATED THREE-DIMENSIONAL MECHANICAL-THERMO-ACOUSTO-SEISMIC-FLOW TESTING METHOD

CROSS-REFERENCE TO RELATED APPLICATIONS

This application claims priority to Chinese Patent Application No. 202310192077.2, filed on Mar. 2, 2023, which is hereby incorporated by reference in its entirety.

TECHNICAL FIELD

The present invention relates to the technical field of rock mechanical behavior testing, and in particular, to a deep rock in situ environment reconstruction and integrated three-dimensional mechanical-thermo-acousto-seismic-flow testing method.

BACKGROUND

China is in the stage of accelerating industrialization and urbanization, and the demand for resources is increasing day by day. The resources in the shallow parts of the earth have gradually been depleted. The deep earth, deep sea and deep space areas contain a large amount of resources and energy, and therefore, the demand for resources and energy is gradually shifting to the deep at present. Due to the unknown and lack of scientific theories in the deep earth area, the implementation of related projects faces huge challenges. For the extraction and utilization of deep earth resources, an extraction environment faces "high stress, high ground temperature, high osmotic pressure" and more severe engineering disturbances, which makes the development of deep resources difficult and costly. Moreover, the disaster accidents are high in frequency, large in magnitude, and difficult to predict, which seriously affects the safe and efficient extraction of deep resources. Therefore, the development of related deep rock physico-mechanical tests has great theoretical, engineering and strategic significance. At present, relevant theories and technologies for the exploration and development of conventional resources in the shallow part of the earth crust are mature; however, theories and technologies for the development and utilization of deep earth resources are lacked, and establishment of theories and technical systems is inseparable from a matched physico-mechanical experiment system.

For the projects of mining of deep mineral resources, geological storage of carbon dioxide, underground space development and geothermal development, the stress environment is a true triaxial stress state due to the effects of tectonic stress, mining disturbance, occurrence environment, formation stress, reservoir water environment and the like, and particularly after the deep areas are reached, the stress has the characteristic of high pressure. An experimental system capable of performing multi-physical field, multi-scale and three-dimensional multi-parameter real-time synchronous monitoring under complex environmental conditions such as high temperature, high pressure and high osmotic pressure is lacked.

SUMMARY

To resolve the foregoing technical problem, the present application provides a deep rock in situ environment reconstruction and integrated three-dimensional mechanical-thermo-acousto-seismic-flow testing method.

The present application is implemented by the following technical solutions.

The deep rock in situ environment reconstruction and integrated three-dimensional mechanical-thermo-acousto-seismic-flow testing method provided by the present application comprises the following steps:

S1: preparing a cubic sample;

S2: placing the cubic sample in a sample holder, wherein the sample holder is provided with ports that are adapted to indenters in upper, lower, left, right, front and rear directions;

S3: respectively extending front ends of the 6 indenters into the sample holder from the ports of the sample holder in 6 directions to contact with six faces of the cubic sample;

wherein the front end of each indenter is provided with a plurality of permeation holes, each indenter is provided with a seepage medium channel, and one end of the percolation medium channel is communicated with the plurality of permeation holes; the front end of the indenter is provided with a temperature sensor, a heat flow sensor, an acoustic emission probe and an ultrasonic probe;

S4: placing the 6 indenters, the cubic sample and the sample holder in a box body, and mounting 6 butting indenters to 6 faces of the box body, wherein the butting indenters can move axially relative to the box body, and front ends of the 6 butting indenters are respectively butted with rear ends of the 6 indenters;

S5: placing the box body on a loading frame beam 92 of a three-axis six-direction loading system, wherein 6 hydraulic actuators of the three-axis six-direction loading system are each butted with a rear end of one of the butting indenters;

S6: making inner edges of the ports of the sample holder in 6 directions in sealing contact with the cubic sample;

S7: comprising:

stress loading: performing stress loading on the cubic sample by using a hydraulic actuator;

filling a fluid medium into the cubic sample through the percolation medium channel;

wherein the following data are dynamically measured: fluid pressure, deformation of the cubic sample, percolation fluid flow, acoustic wave data and acoustic emission data.

Optionally, the box body is provided with an air inlet, an air outlet and a cold source port; if a high-temperature environment is required during the experiment, hot air is sent into the box body through the air inlet; and if a low-temperature environment is required, liquid nitrogen is injected into the box body through the cold source port.

Particularly, the sample holder comprises a rigid outer cubic frame and a flexible inner cubic frame, the rigid outer cubic frame and the flexible inner cubic frame are both provided with 12 frame edges, 6 faces of the rigid outer cubic frame and 6 faces of the flexible inner cubic frame are both rectangular frames, 12 outside corner positions of the flexible inner cubic frame are attached to 12 inside corners of the rigid outer cubic frame, and the cubic sample is loaded in the flexible inner cubic frame; and in the S6, inner edges of rectangular openings of the flexible inner cubic frame in 6 directions are in sealing contact with the cubic sample.

Particularly, the front end of the indenter is provided with an annular groove, a circumferential sealing strip is embedded in the annular groove, a sealing medium injection channel is provided in the indenter, one end of the sealing medium injection channel is communicated with the annular groove, and the other end of the sealing medium injection channel is connected to a hydraulic sealing system; each face of the flexible inner cubic frame is provided with an integrally-manufactured annular flange, and the annular flange is adapted to an annular sealing groove of the circumferential sealing strip;

in the S3, when the front ends of 6 indenters respectively extend into the sample holder from the ports of the sample holder in 6 directions to contact with six faces of the cubic sample, the annular flanges are correspondingly mounted in the annular sealing grooves of the circumferential sealing strips on the 6 indenters; in the S6, the percolation medium channels of all the indenters are closed, and a sealing medium is injected into the sealing medium injection channels of the 6 indenters through the sealing system, so that 12 edges of the cubic sample are tightly attached to the flexible inner cubic frame, and a three-way sealing is achieved.

Optionally, the indenter comprises an indenter body and a permeation block, a front end of the indenter body is provided with an annular groove and a rectangular convex block, the annular groove is located at an edge of the front end of the indenter body, and the rectangular convex block is located on an inner periphery of the annular groove; a front end face of the rectangular convex block is provided with an integrally-manufactured embedding groove, the permeation block is embedded in the embedding groove, a plurality of permeation holes are provided on the permeation block, and the permeation holes are communicated with the permeation block from front to back; and a percolation medium channel and a sealing medium injection channel are provided in the indenter body, one end of the percolation medium channel is communicated with the embedding groove, and the other end of the sealing medium injection channel and the percolation medium channel is communicated with an outer surface of the indenter body.

Optionally, a displacement detection mechanism is provided between the two indenters in the same axial direction, and the deformation of the cubic sample is monitored by the displacement detection mechanism.

Optionally, the hydraulic actuator comprises a cylinder barrel, a piston and an actuating indenter, the actuating indenter is connected to a free end of the piston, and the actuating indenters of the 6 hydraulic actuators are each configured to adapt to the rear end of one of the butting indenters; and a first displacement sensor is arranged between the cylinder barrel and the piston, and a force sensor is arranged between the actuating indenter and the piston.

Particularly, in the S3, after 6 indenters are butted with the sample holder, 12 elastic pieces are used to connect the 6 indenters together, so that the cubic sample, the sample holder and the 6 indenters form a whole, and a periphery of each indenter is connected to 4 indenters on the periphery through one elastic piece.

Compared with the prior art, the present application has the following beneficial effects:

1. the present application can achieve three-way multi-parameter synchronous monitoring and acquisition of deformation, acoustic emission, ultrasonic waves, a temperature field, a percolation field and a heat flow field, and has great significance for the construction of a new deep underground engineering science theory, the evaluation of deep resources, the research and development of basic theories and technologies such as exploitation and application and the like; and 2. according to the present application, hot air is introduced into the box body through the air inlet to provide a high-temperature environment for the sample, and a cold source can be injected into the box body through the cold source port to provide a low-temperature environment for the sample; therefore, rock physicomechanical experiments can be performed in real-time under high-temperature and low-temperature environments.

BRIEF DESCRIPTION OF DRAWINGS

The drawings illustrated herein are used to provide a further understanding of the embodiments of the present application, constitute a part of the present application, and do not constitute a limitation to the embodiments of the present invention.

Figure 1:
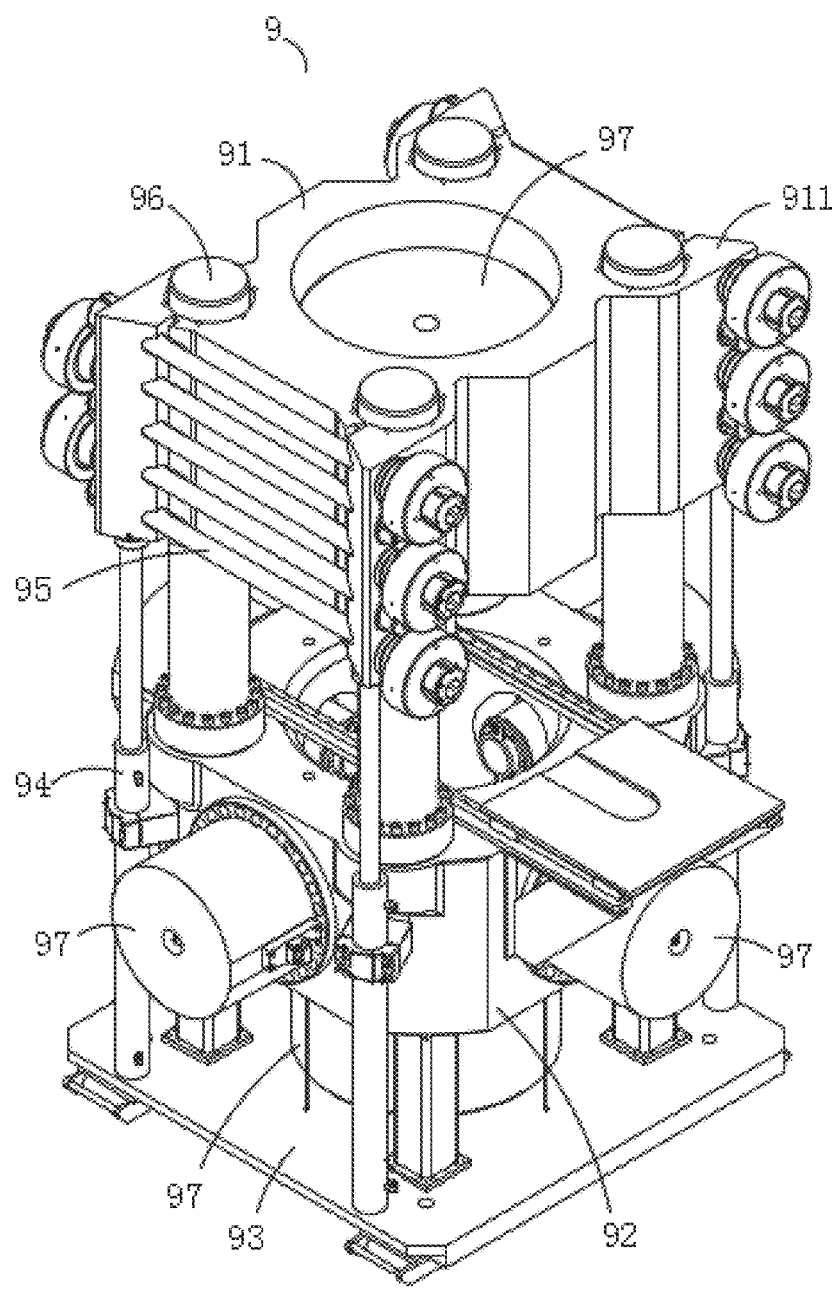
FIG. 1 is a three-dimensional view of a three-axis six-direction loading system according to an embodiment.

in the drawings: 1: box body, 10: cubic sample, 11: outer cubic frame, 12: wall plate, 13: elastic plate, 14: aviation connector area, 121: flange, 122: clearance notch, 131: strip-shaped notch;

2: butting indenter;

31: air inlet, 32: air outlet, 33: cold source port;

41: percolation inlet pipe, 42: percolation outlet pipe, 43: sealing main pipe, 45: sealing branch pipe;

5: elastic pressure box, 51: indenter, 52: elastic piece, 53: thermal conductive pad, 54: butting port, 55: temperature sensor, 56: heat flow sensor, 57: circumferential sealing strip, 58: acoustic emission probe, 59: ultrasonic probe, 501: annular groove, 502: embedding groove, 511: indenter body, 512: permeation block, 513: rectangular convex block, 514: percolation medium channel, 515: sealing medium injection channel, 516: permeation hole, 571: annular sealing groove;

6: displacement detection mechanism, 61: first connection arm, 62: second connection arm, 66: second displacement sensor, 67: extensometer rod;

7: sample holder, 71: rigid outer cubic frame, 72: flexible inner cubic frame, 701: port, 702: rectangular opening, 721: frame edge, 722: annular flange, 723: outside corner position, 724: right-angle edge structure;

8: electric heating plate;

9: three-axis six-direction loading system, 91: vertical moving beam, 92: loading frame beam, 93: base, 94: lift hydraulic cylinder, 95: clamping hydraulic cylinder, 96: bearing column, 97: hydraulic actuator, 911: clamping arm, 951: pull rod, 952: hydraulic locking cylinder, 953: locking nut, 954: thrust joint bearing, 971: cylinder barrel, 972: piston, 973: actuating indenter, 974: first displacement sensor, 975: force sensor; and 100: hydraulic sealing system, 200: vacuumizing device.

DESCRIPTION OF EMBODIMENTS

To make objectives, technical solutions, and advantages of the present application clearer, the following clearly and completely describes technical solutions in embodiments of the present invention with reference to accompanying drawings in embodiments. It is clear that the described embodiments are merely some but not all of embodiments of the present invention. Generally, components of embodiments of the present invention described and shown in the accompanying drawings herein may be arranged and designed in various configurations.

Therefore, the following detailed descriptions of embodiments of the present invention provided in the accompanying drawings are not intended to limit the scope of the present invention that claims protection, but merely to represent selected embodiments of the present invention. Based on the embodiments of the present invention, all other embodiments obtained by those of ordinary skill in the art without creative effort shall fall within the protection scope of the present invention.

In the description of the present invention, it should be noted that an orientation or position relationship indicated by terms "upper", "lower", "inner", "outer", or the like is an orientation or position relationship based on the accompanying drawings, or an orientation or position relationship that the product of the present invention is usually placed when in use, or an orientation or positional relationship commonly understood by those skilled in the art. These terms are merely used to facilitate and simplify description of the present invention, instead of indicating or implying that a mentioned apparatus or element must have a specific orientation or be constructed and operated in a specific orientation, and therefore the terms cannot be construed as a limitation on the present invention.

In descriptions of the present invention, it should be further noted that, unless otherwise expressly specified and limited, terms "arranged", "mount", "interconnect" and "connect" should be understood in a broad sense. For example, such terms may indicate a fixed connection, a detachable connection, or an integral connection; may indicate a mechanical connection or an electrical connection; and may indicate direct interconnection, indirect interconnection through an intermediate medium, or internal communication between two elements. For those of ordinary skill in the art, the specific meanings of the aforementioned terms in the present invention can be understood according to specific conditions.

Embodiment 1

As shown in FIG. 1, the deep rock in situ environment reconstruction and integrated three-dimensional mechanical-thermo-acousto-seismic-flow testing method disclosed in this embodiment is implemented based on a multi-field multi-parameter integrated rock three-dimensional mechanical-thermo-acousto-seismic-flow testing system. Firstly, a multi-field multi-parameter integrated rock three-dimensional mechanical-thermo-acousto-seismic-flow testing system is illustrated, and the system comprises an experimental cabin and a three-axis six-direction loading system.

Figure 2:
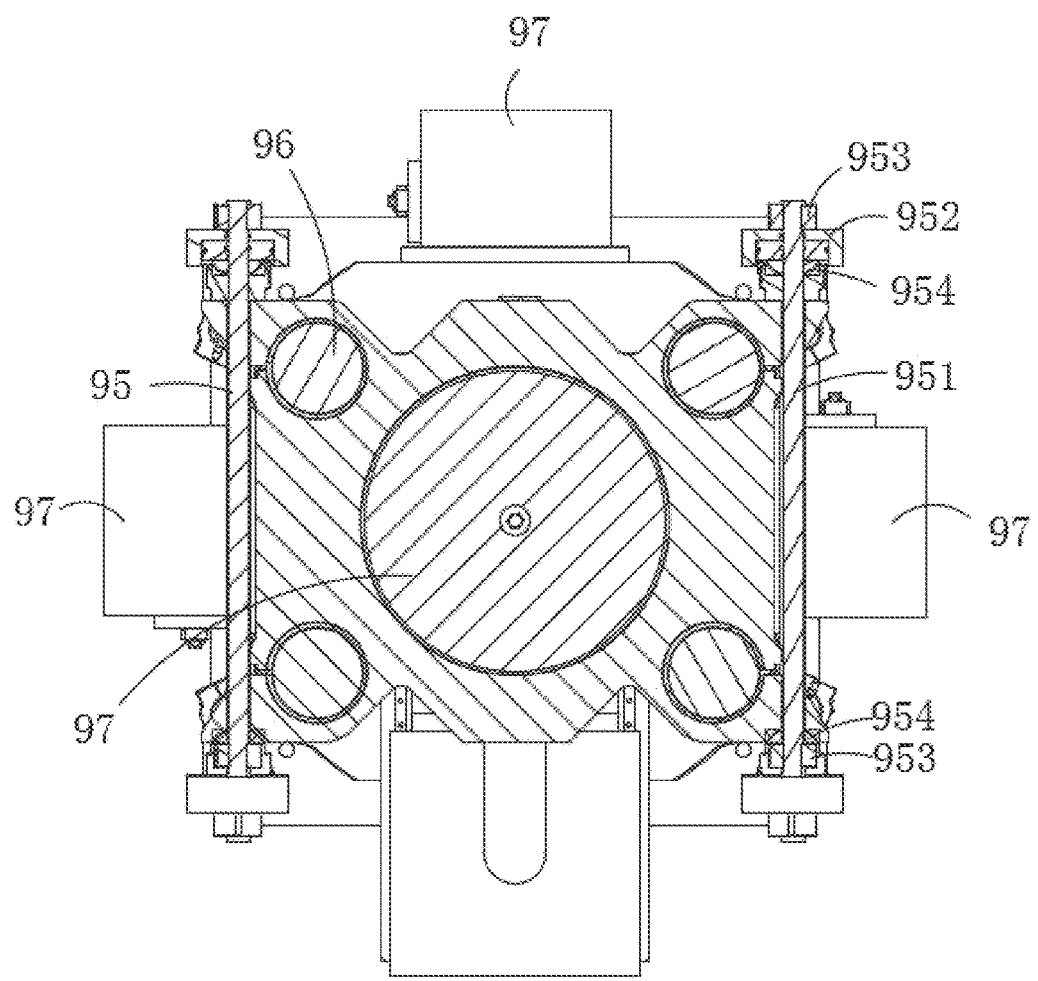
FIG. 2 is a front view of a three-axis six-direction loading system according to an embodiment at the tensioning cylinder.
Figure 3:
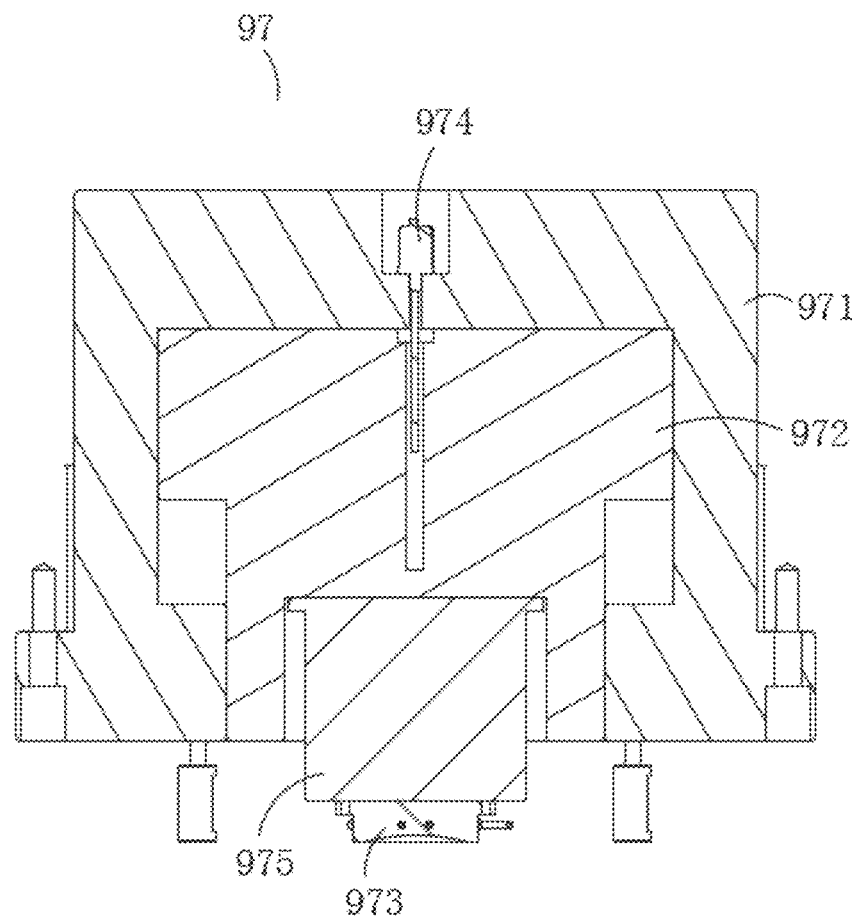
FIG. 3 is a schematic diagram of a structure of a hydraulic actuator according to an embodiment.

As shown in FIGS. 1 to 3, the three-axis six-direction loading system 9 is configured to provide true triaxial stress to a sample. Specifically, the three-axis six-direction loading system 9 comprises a high-pressure oil pump station, a beam assembly, a lift hydraulic cylinder 94, a loading frame beam 92 and six hydraulic actuators 97. The six hydraulic actuators 97 are pairwise located in an X-axis direction, a Y-axis direction and a Z-axis direction. It should be noted that the X axis, the Y axis and the Z axis herein refer to an X axis, a Y axis and a Z axis in a three-axis coordinate system, respectively.

The loading frame beam 92 is an integrally cast high-rigidity structure, and the loading frame beam 92 is fixedly connected to the base 93 through a plurality of support legs. An experimental cabin accommodation chamber for accommodating the experimental cabin is provided in a center of the loading frame beam 92, the experimental cabin accommodation chamber passes through a top surface of the loading frame beam 92, and the experimental cabin can be placed into the accommodation chamber from top to bottom, and also serves as a loading port for the upper hydraulic actuator 97 to apply vertical stress.

The front, rear, left, right and lower sides of the loading frame beam 92 are each provided with a loading port, and the loading port is communicated with the experimental cabin accommodation chamber. The hydraulic actuators 97 in the X-axis and Y-axis directions and the lower hydraulic actuator 97 in the Z-axis direction are respectively mounted at 5 loading ports of the loading frame beam 92.

In a possible design, the beam assembly comprises a vertical moving beam 91, a bearing column 96 and a beam locking mechanism, and an upper hydraulic actuator 97 in the Z-axis direction is mounted on a center of the vertical moving beam 91. A lower end of the bearing column 96 is fixed with the loading frame 92 through the bearing nut, the vertical moving beam 91 is mounted on 4 bearing columns 96, the lift hydraulic cylinder 94 is supported between the loading frame beam 92 and the vertical moving beam 91, the beam moving mechanism 94 is configured to achieve the up-and-down movement of the vertical moving beam 91 along the bearing column 96, and the vertical moving beam 91 and the plurality of bearing columns 96 may be fixed through the beam locking mechanism.

In a possible design, the vertical moving beam 91 is provided with four clamping openings, 4 bearing columns 96 are each mounted in one of the clamping openings, and the vertical moving beam 91 and the bearing columns 96 are clamped by a beam locking mechanism. Particularly, the beam locking mechanism comprises two sets of clamping hydraulic cylinders 95, an extended clamping arm 911 is arranged outside each clamping opening, and the clamping arms 911 of every two clamping openings are tensioned through one set of clamping hydraulic cylinders 95 so as to simultaneously clamp and fix two corresponding bearing columns 96 and the vertical moving beam 91.

Optionally, as shown in FIG. 2, the clamping hydraulic cylinder 95 comprises a pull rod 951, a hydraulic locking cylinder 952 and a locking nut 953. The hydraulic locking cylinder 952, the locking nut 953 and the thrust joint bearing 954 are all mounted on a pull rod 951. Two ends of the pull rod 951 are respectively arranged in the holes corresponding to the two clamping arms 911, two ends of the pull rod 951 are provided with locking nuts 953, a thrust joint bearing 954 is arranged between the locking nut 953 at one end and the clamping arm 911, a hydraulic locking cylinder 952 is arranged between the locking nut 953 at the other end and the other clamping arm 911, and a thrust joint bearing 954 is arranged between the hydraulic locking cylinder 952 and the other clamping arm 911.

In a possible design, as shown in FIG. 3, the hydraulic actuator 97 comprises a cylinder 971, a piston 972 and an actuating indenter 973, a first displacement sensor 974 is provided between the cylinder 971 and the piston 972, and the actuating indenter 973 is connected to a free end of the piston 972. A servo valve is mounted on the cylinder 971, and a force sensor 975 is provided between the actuating indenter 973 and the piston 972.

The present application can meet the monitoring and control of a range of the actuator through the first displacement sensor 974. Optionally, the first displacement sensor 974 is a magnetostrictive displacement sensor, which can meet a range of the actuator.

A strain gauge is welded on an end part of the actuating indenter 973 to monitor the force of the hydraulic actuator. The three-axis six-direction loading system 9 according to the present application has control methods such as force and displacement, and can achieve independent work and linkage coordination work of six pressure cylinders. According to the present application, smooth transition among force loading, displacement loading and control can be achieved, and data such as stress, displacement, strain and the like can be precisely recorded in real time.

Figure 4:
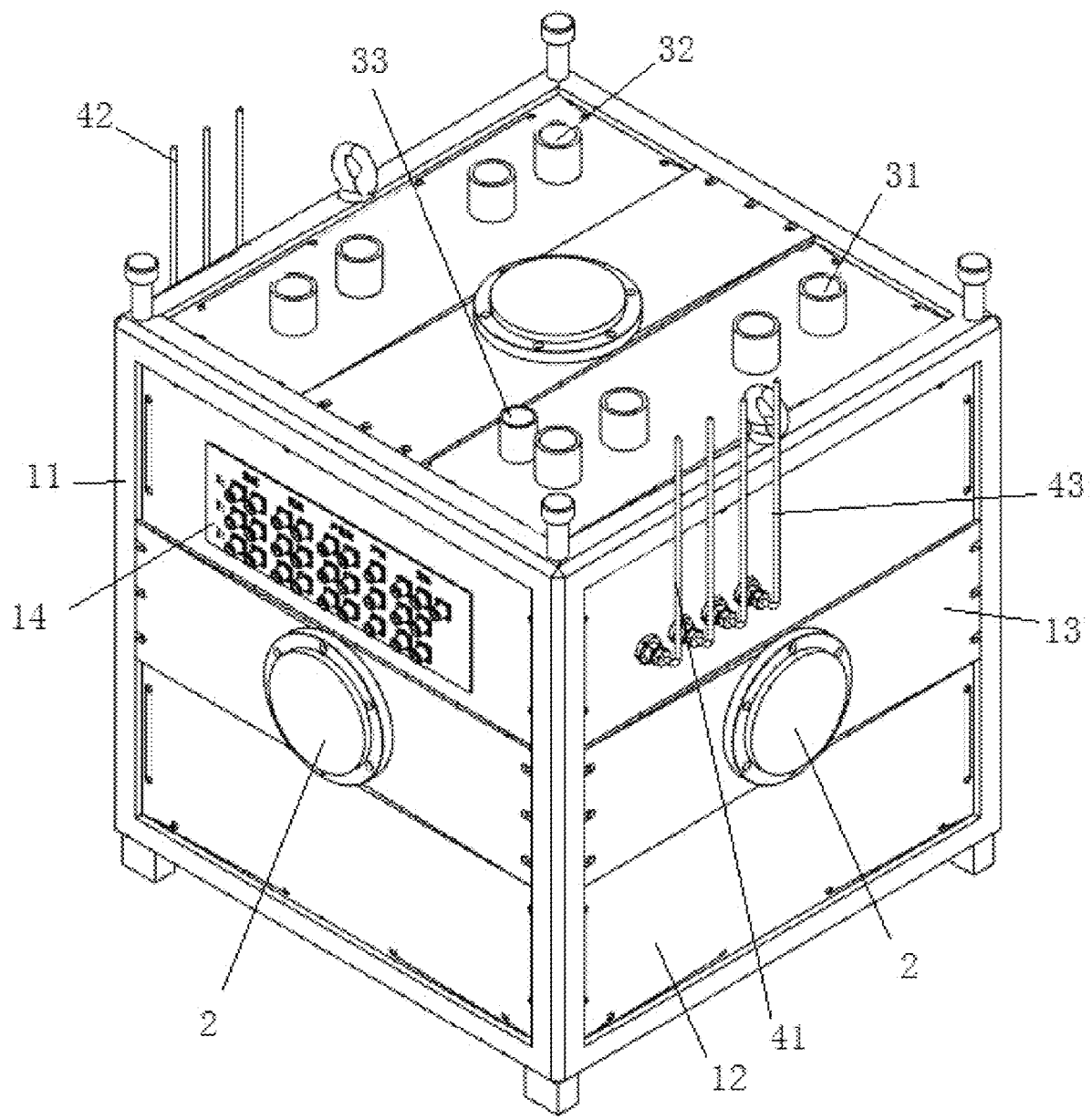
FIG. 4 is a three-dimensional view of an experimental cabin according to an embodiment.
Figure 5:
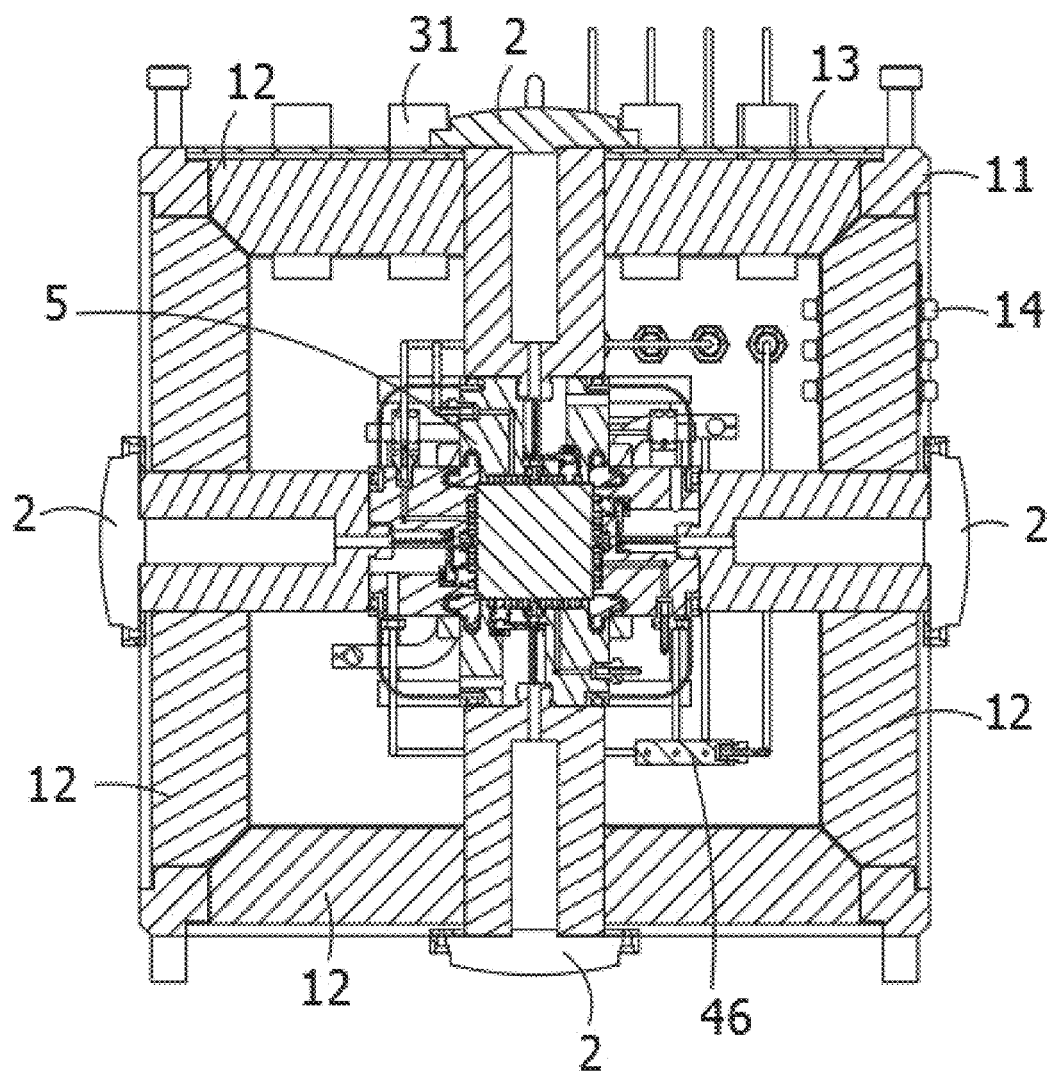
FIG. 5 is a cross-sectional view of an experimental cabin according to an embodiment.

As shown in FIGS. 4 and 5, the experimental cabin in this embodiment comprises: a box body 1, 6 butting indenters 2, an elastic pressure box 5 and a sample holder 7, wherein the elastic pressure box 5 can be accommodated in the box body 1.

Figure 9:
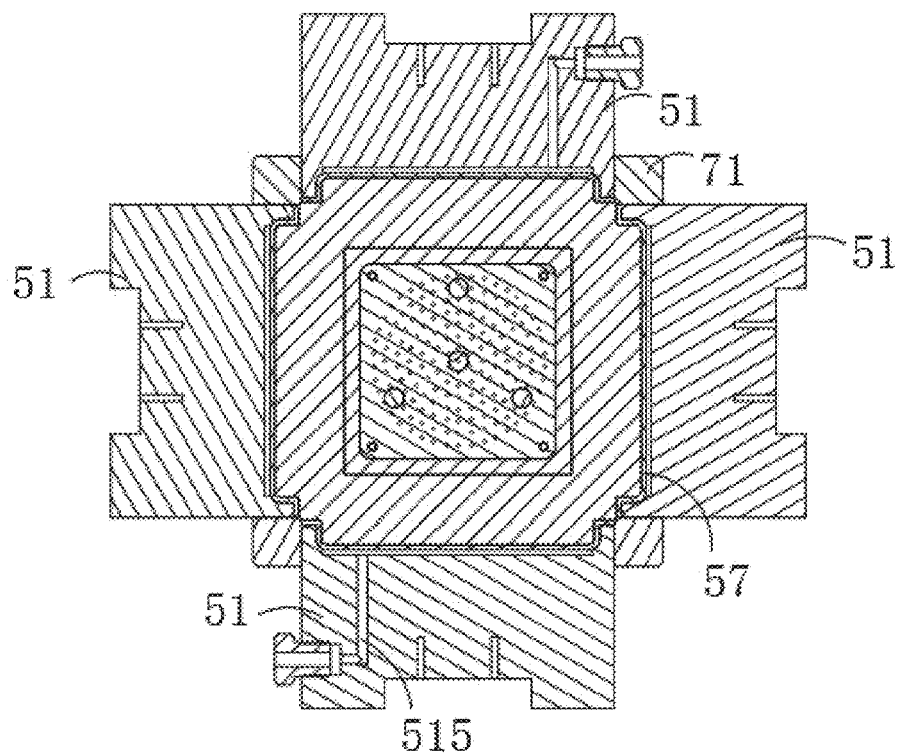
FIG. 9 is a cross-sectional view at B-B in FIG. 7.
Figure 10:
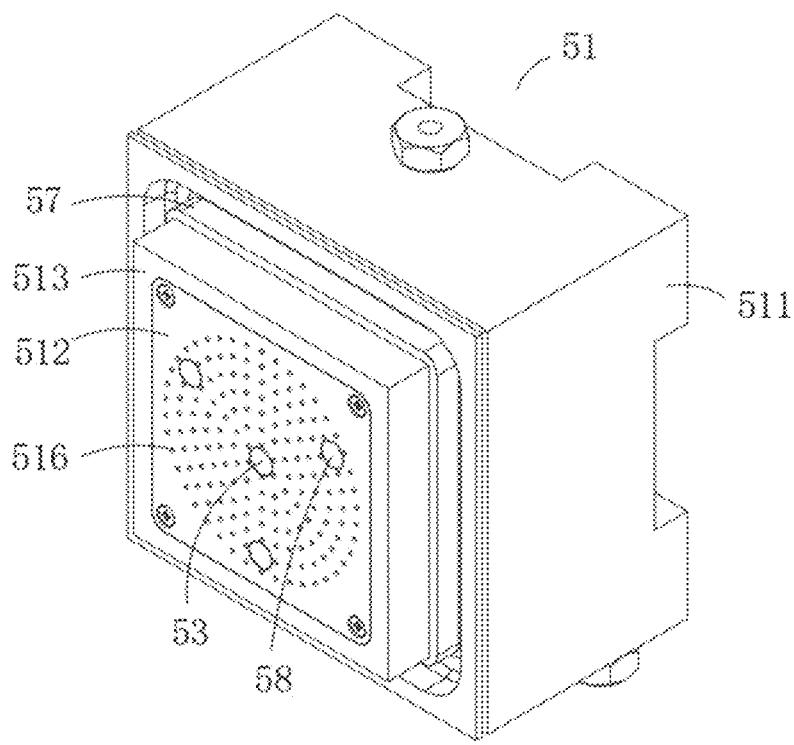
FIG. 10 is a three-dimensional view of an indenter according to an embodiment.

As shown in FIGS. 5 and 9, the elastic pressure box 5 comprises 6 indenters 51, and the 6 indenters 51 are respectively configured to contact with 6 faces of the cubic sample 10.

In a possible design, as shown in FIGS. 8 to 12, the indenter 51 comprises an indenter body 511 and a permeation block 512. A front end of the indenter body 511 is provided with an integrally-manufactured annular groove 501 and a rectangular convex block 513, the annular groove 501 is located at an edge of the front end of the indenter body 511, the rectangular convex block 513 is located on an inner periphery of the annular groove 501, and a circumferential sealing strip 57 is embedded in the annular groove 501. A percolation medium channel 514 and a sealing medium injection channel 515 are arranged in the indenter body 511, one end of the sealing medium injection channel 515 is communicated with the annular groove 501 of the indenter body 511, and the other end of the sealing medium injection channel passes through an outer surface of the indenter body 511.

A front end face of the rectangular convex block 513 is provided with an integrally-manufactured embedding groove 502, the permeation block 512 is embedded in the embedding groove 502 through screws, a plurality of permeation holes 516 are uniformly distributed in the permeation block 512, and the permeation holes 516 are communicated with the permeation block 512 from front to back. One end of the percolation medium channel 514 is communicated with the embedding groove 502, and the other end of the percolation medium channel is communicated with the outer surface of the indenter body 511. Percolation media with different temperatures and pressures can be injected through the percolation medium channel 514 according to experimental requirements, and the percolation media flow into the embedding groove 502 and then uniformly flow to the sample through a plurality of permeation holes 516. A high-pressure sealing medium can be injected into the annular groove 501 through the sealing medium injection channel 515, so that percolation medium can be prevented from flowing out from an edge of the sample, which can be used for rock mass percolation testing.

Figure 11:
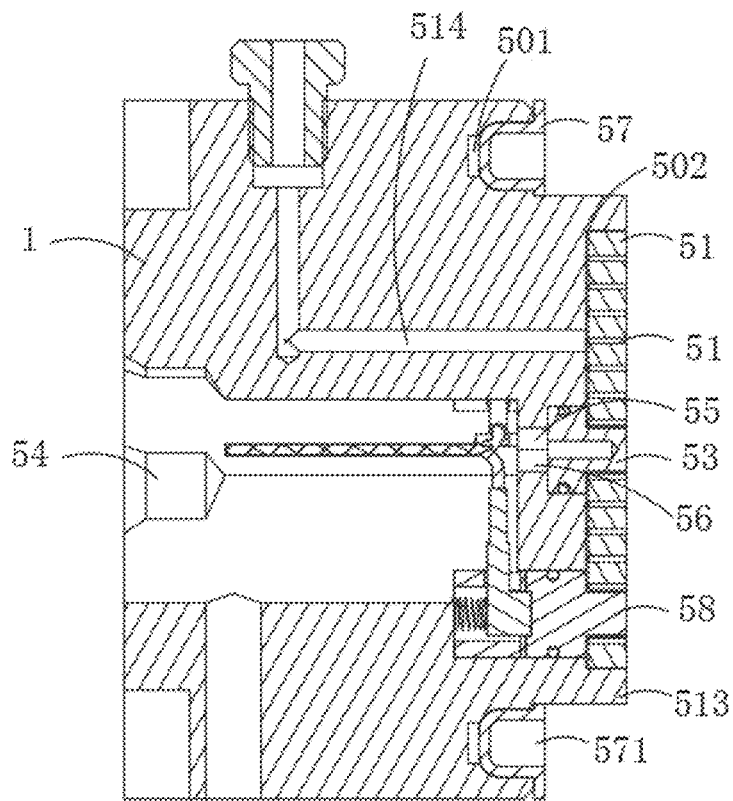
FIG. 11 is a cross-sectional view of an indenter according to an embodiment in a first section.
Figure 12:
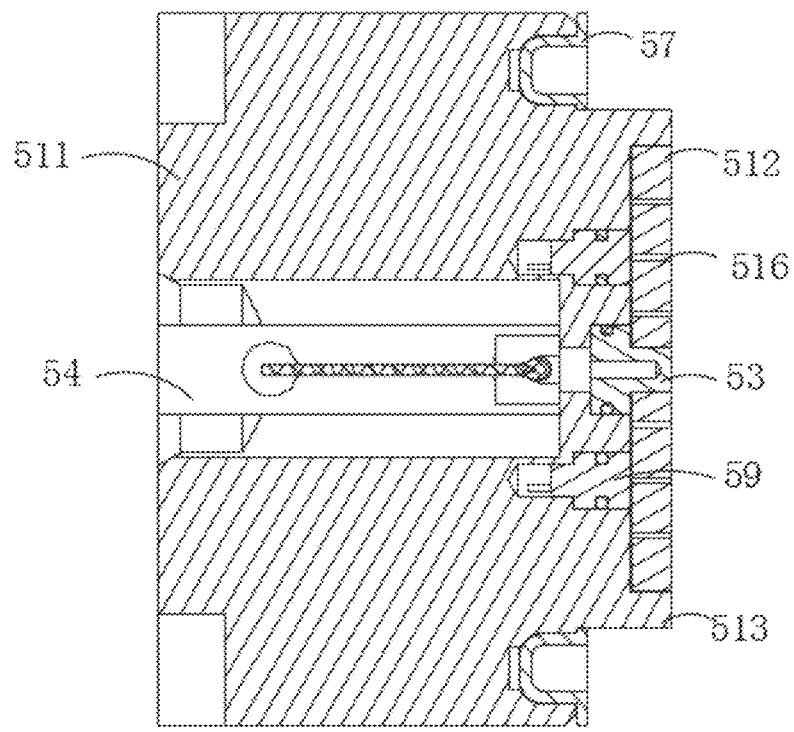
FIG. 12 is a cross-sectional view of an indenter according to an embodiment in a second section.

As shown in FIGS. 11 and 12, the front end of the indenter 51 is provided with an acoustic emission probe 58 that is resistant to high temperature and high pressure, an ultrasonic probe 59, a temperature sensor 55 and a heat flow sensor 56, and a center of the back of the indenter 51 is provided with a butting port 54.

In a possible design, the acoustic emission probe 58 is mounted in the acoustic emission probe mounting hole of the front end of the indenter 51, and a sealing ring is provided between the acoustic emission probe 58 and the indenter 51. Particularly, the front end of the indenter 51 is provided with three acoustic emission probes 58, and the three acoustic emission probes 58 are arranged at equal intervals in the circumferential direction around a center of the indenter 51.

In a possible design, the indenter 51 is provided with two ultrasonic probes 59, one of which is a P-wave and the other is an S-wave. The ultrasonic probe 59 is mounted in the ultrasonic wave emission probe mounting hole of the front end of the indenter 51, and a sealing ring is provided between the ultrasonic probe 59 and the indenter 51.

In a possible design, the front end of each indenter 51 is provided with 3 sets of high-temperature and high-pressure acoustic emission probes with a frequency of 20-1200 kHz and a sampling frequency of 10 Hz, and real-time monitoring of microseismic signals in the rock mass fracture process can be achieved. Optionally, 2 sets of high-temperature and high-pressure acoustic emission probes integrate one P wave and one S wave respectively for ultrasonic detection function, which can achieve real-time monitoring of ultrasonic waves during the experiment.

Particularly, an integrated temperature and heat flow probe is embedded in a center hole of each indenter 51. The real-time monitoring of the surface temperature of the sample in the experimental process can be achieved, and the heat flow can be measured. A thermal conductive pad 53 is mounted at a front end of the center hole of the indenter 51, and the temperature of the sample is transmitted to the integrated temperature and heat flow probe in the center hole through the thermal conductive pad 53. A sealing ring is arranged between the thermal conductive pad 53 and the indenter 51.

Figure 13:
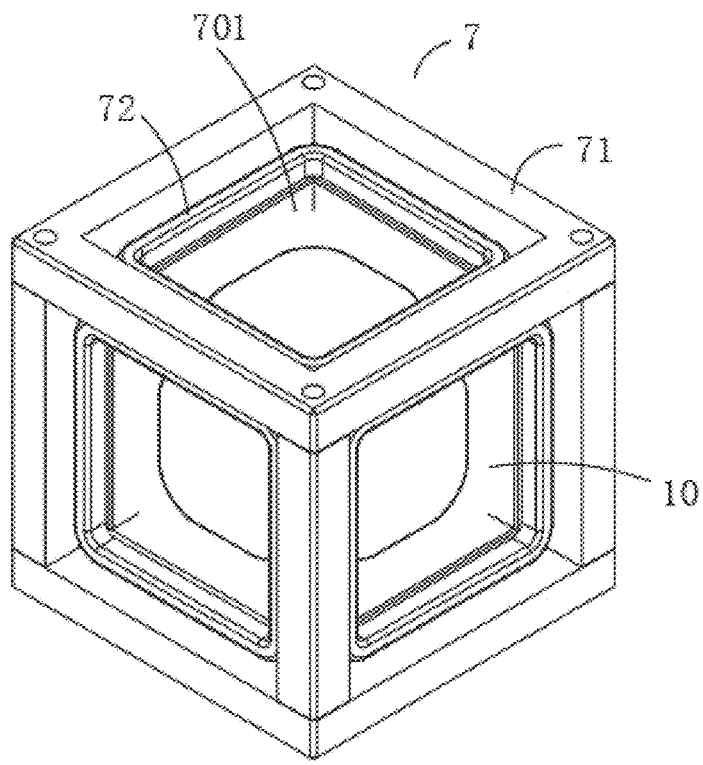
FIG. 13 is a three-dimensional view of a sample holder according to an embodiment.
Figure 14:
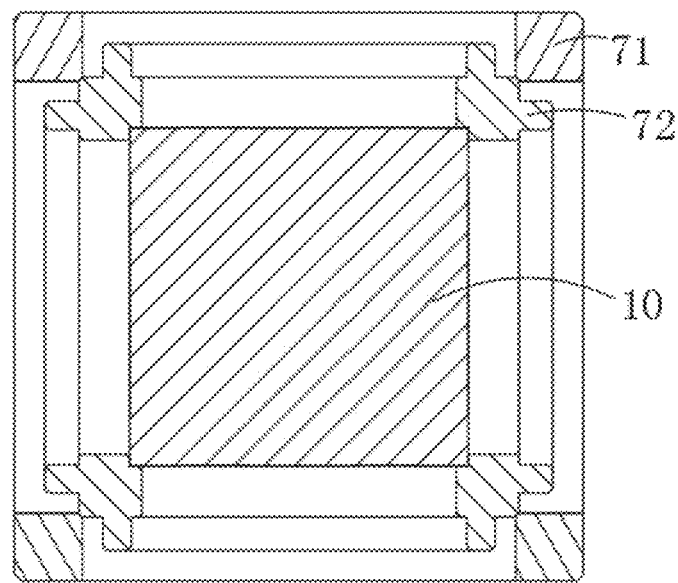
FIG. 14 is a cross-sectional view of a sample holder according to an embodiment.

As shown in FIGS. 13 and 14, the sample holder 7 is configured to fix a cubic sample 10; meanwhile, ports 701 adapted to 6 indenters 51 need to be reserved in 6 directions.

In a possible design, the sample holder 7 comprises a rigid outer cubic frame 71 and a flexible inner cubic frame 72, the rigid outer cubic frame 71 and the flexible inner cubic frame 72 are both provided with 12 frame edges 721, 6 faces of the rigid outer cubic frame 71 and 6 faces of the flexible inner cubic frame 72 are both rectangular frames, and rectangular openings 702 are provided in 6 directions. The 12 outside corner positions 723 of the flexible inner cubic frame 72 are attached to 12 inside corners of the rigid outer cubic frame 71, and the cubic sample 10 may be loaded in the flexible inner cubic frame 72.

In a possible design, the 12 inside corner positions of the flexible inner cubic frame 72 have right-angled edge structures 724 that are adapted to corners of the cubic sample 10.

Figure 15:
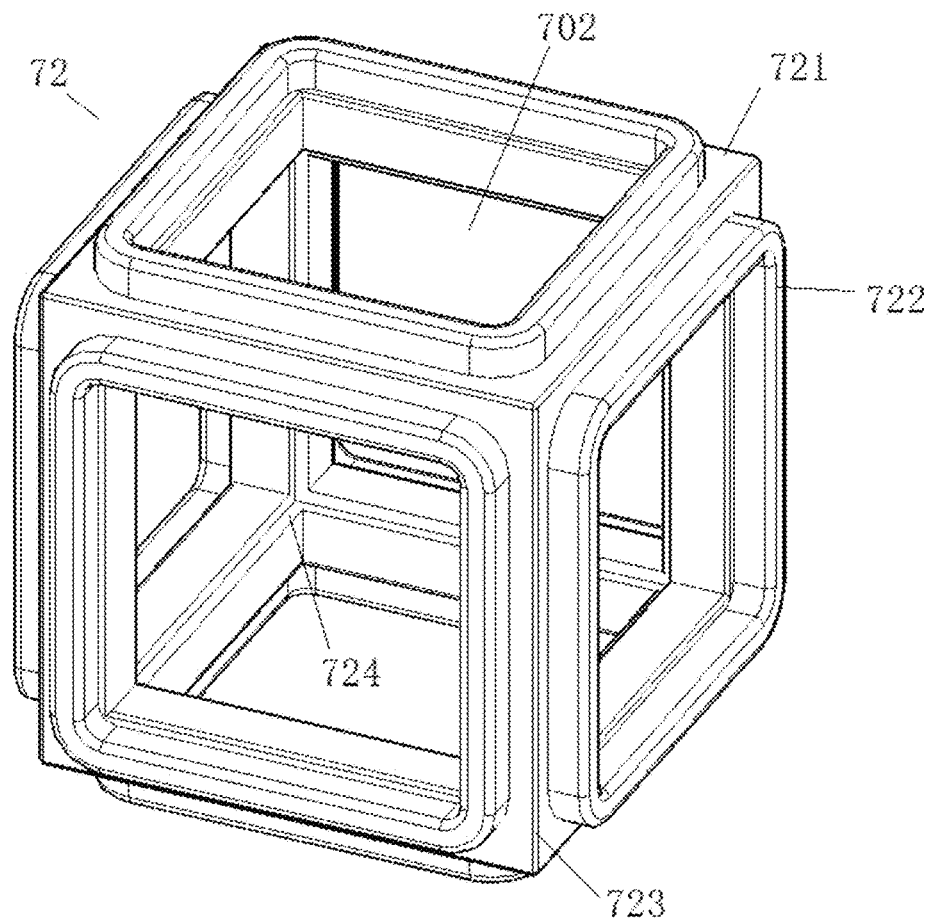
FIG. 15 is a three-dimensional view of a flexible inner cubic frame according to an embodiment.
Figure 16:
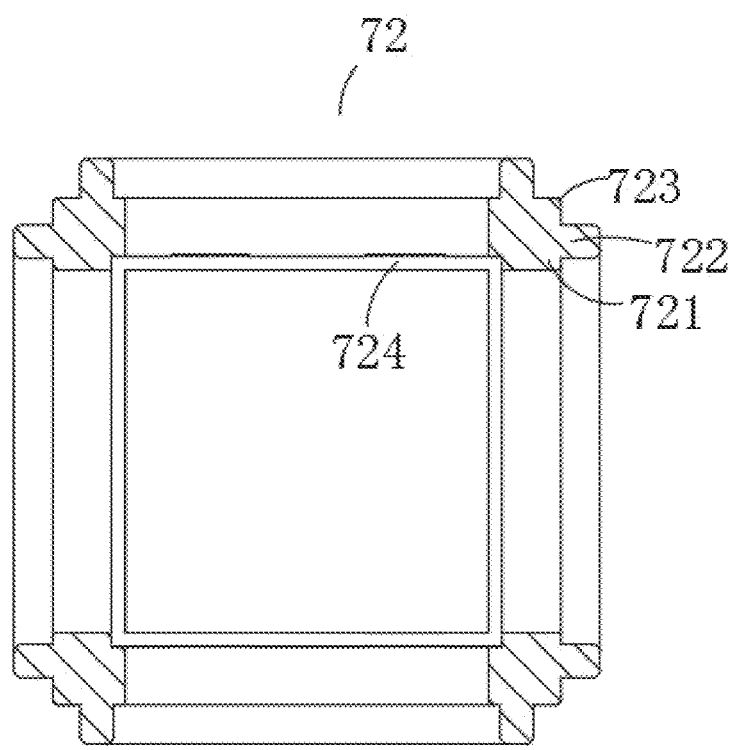
FIG. 16 is a cross-sectional view of a flexible inner cubic frame according to an embodiment.

In a possible design, as shown in FIGS. 15 and 16, each face of the flexible inner cubic frame 72 is provided with an integrally-manufactured annular flange 722. As shown in FIG. 11, the circumferential sealing strip 57 is provided with an annular sealing groove 571 that is adapted to the annular flange 722, and the annular flange 722 can be fitted in the annular sealing groove 571 of the circumferential sealing strip 57.

Optionally, the flexible inner cubic frame 72 is made of a wear-resistant, pressure-resistant and high-strength rubber frame, the rigid outer cubic frame 71 is a metal frame, and the circumferential sealing strip 57 is made of high-strength rubber.

In a possible design, the indenter 51 is rectangular, the indenter 51 is adapted to a rectangular frame opening of the rigid outer cubic frame 71, and the indenter and the rectangular frame opening of the rigid outer cubic frame may be kept relatively fixed by friction or may be fixed with each other by providing a clamping groove. A rectangular convex block 513 is adapted to a rectangular frame opening of the flexible inner cubic frame 72.

As shown in FIG. 4, the box body 1 is a hexahedral structure, each face of the box body is provided with one butting indenter 2, and 6 butting indenters 2 are pairwise located in an X-axis direction, a Y-axis direction and a Z-axis direction. The 6 butting indenters 2 are respectively arranged in through holes of the box body 1 on six surfaces and can move axially relative to the box body 1, and the front ends of the butting indenters 2 extend into the box body 1 and are used for butt with the rear ends of indenters 51 of the elastic pressure box 5; the rear ends of the butting indenters are exposed out of the box body 1 and are used to butt with an actuating indenter 973 of the hydraulic actuator 97.

In a possible design, the box body 1 is provided with an air inlet 31, an air outlet 32 and a cold source port 33, and hot air is sent into the box body 1 through the air inlet 31 to heat the box body; and cold source is injected into the box body 1 through the cold source port 33 to reduce the temperature. For example, the temperature is reduced by injecting liquid nitrogen into the box body 1 through the cold source port 33; and a part of the injected liquid nitrogen becomes gas and may be discharged from the air inlet 31 and the air outlet 32.

In a possible design, the box body 1 comprises an outer cubic frame 11 and 6 wall plates 12, wherein the 6 wall plates 12 are mounted in 6 directions of the outer cubic frame 11 through screws, and the 6 wall plates 12 are integrally mounted through the outer cubic frame 11 with high rigidity, so that the stability of the whole system can be guaranteed. The wall plate 12 is preferably of a thermal insulation material. 6 butting indenters 2 are each arranged at a center of one of the wall plates 12.

In a possible design, the air inlet 31, the air outlet 32 and the cold source port 33 are all arranged at the wall plate 12 of the top of the box body 1.

In a possible design, an outer side of each wall plate 12 is provided with an elastic plate 13, coaxial through holes are formed in the elastic plate 13 and the wall plate 12, the butting indenters 2 are mounted in the through holes, the butting indenters 2 are fixedly connected to the elastic plate 13 through screws, and a gap is formed between the elastic plate 13 and an outer surface of the wall plate 12, so that the elastic plate 13 and the butting indenters 2 can axially move inwards by a distance relative to the wall plate 12.

Figure 17:
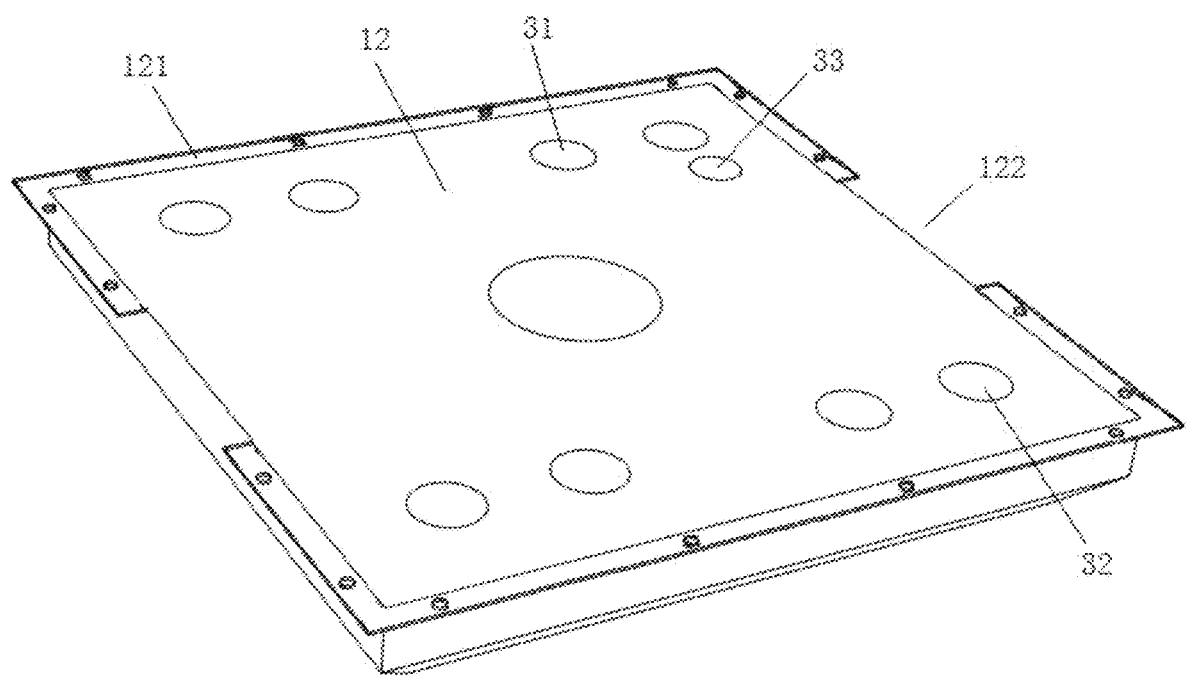
FIG. 17 is a three-dimensional view of a wall plate at a top of the box body according to an embodiment.

Optionally, as shown in FIGS. 4, 5 and 17, sinking grooves are respectively provided at edges of frame openings of the outer cubic frame 11 in six directions, flanges 121 adapted to the sinking grooves are provided at edges of an outer surface of the wall plate 12, and the flanges 121 are attached to the sinking grooves and fixedly connected thereto by screws. Particularly, the flange 121 is broken at a position corresponding to the elastic plate 13, thereby forming a clearance notch 122.

Figure 18:
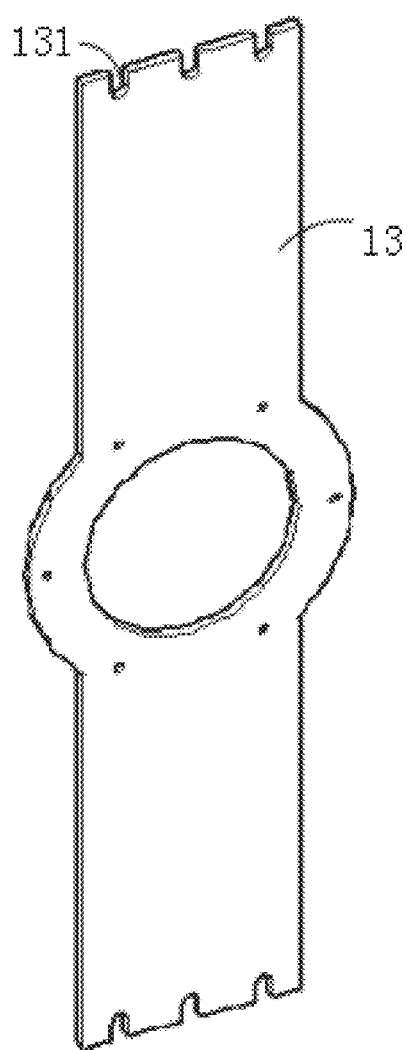
FIG. 18 is a three-dimensional view of an elastic plate according to an embodiment.

Optionally, as shown in FIG. 18, at least two strip-shaped notches 131 are formed at two ends of the elastic plate 13, adapted screws are mounted at a position that is of the outer cubic frame 11 and that corresponds to the strip-shaped notches 131, two ends of the elastic plate 13 are respectively clamped on the screws through the strip-shaped notches 131, so that the elastic plate 13 is movably connected to the outer cubic frame 11, and the screws can slide in the strip-shaped notches 131 under the action of an axial external force.

In a possible design, three percolation inlet pipes 41 are respectively connected to the percolation medium channels 514 of one of the indenters 51 in the X-axis direction, one of the indenters 51 in the Y-axis direction and one of the indenters 51 in the Z-axis direction, and inlet ends of three percolation outlet pipes 42 are respectively connected to the percolation medium channels 514 of the other indenter 51 in the X-axis direction, the other indenter 51 in the Y-axis direction and the other indenter 51 in the Z-axis direction. The three percolation inlet pipes 41 are connected to an external plunger pump, stop valves are respectively arranged on the three percolation inlet pipes 41 and the three percolation outlet pipes 42, flow meters are respectively arranged at the outlets of the three percolation outlet pipes 42, and the flow rate of the fluid can be monitored in real time through the flow meters.

In a possible design, the sealing main pipe 43 is connected to the sealing medium injection channels 515 of the 6 indenters 51 through 6 sealing branch pipes 45, the sealing main pipe 43 is connected to a high-pressure plunger pump, the high-pressure plunger pump can provide 60 MPa sealing pressure, and the sealing main pipe 43 is provided with a valve.

Figure 6:
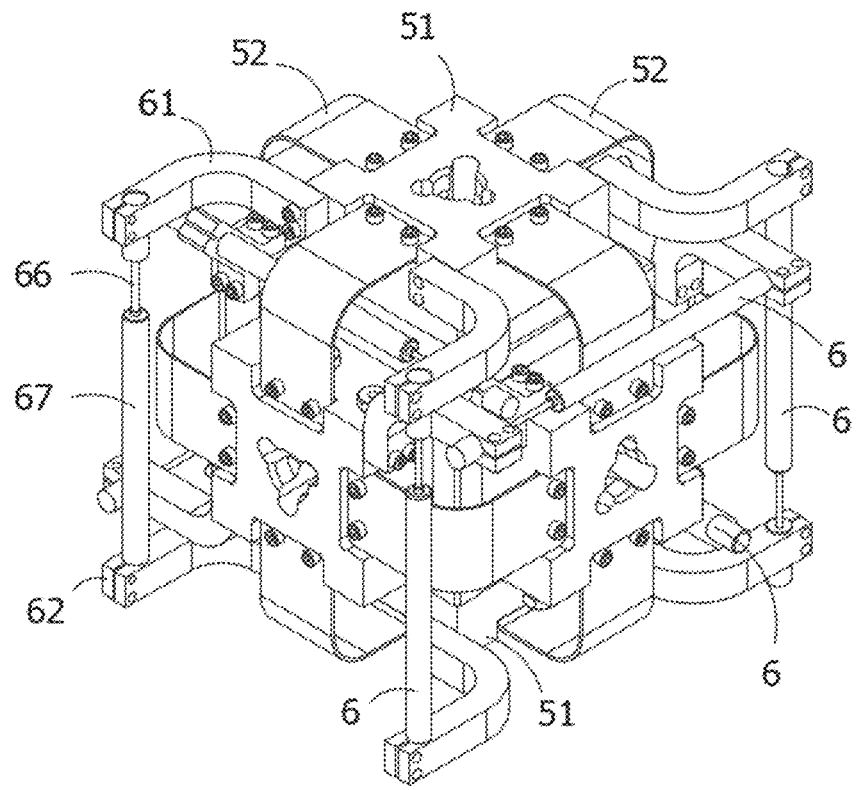
FIG. 6 is a three-dimensional view of an elastic pressure box according to an embodiment when a displacement detection mechanism is provided between each pair of indenters.
Figure 7:
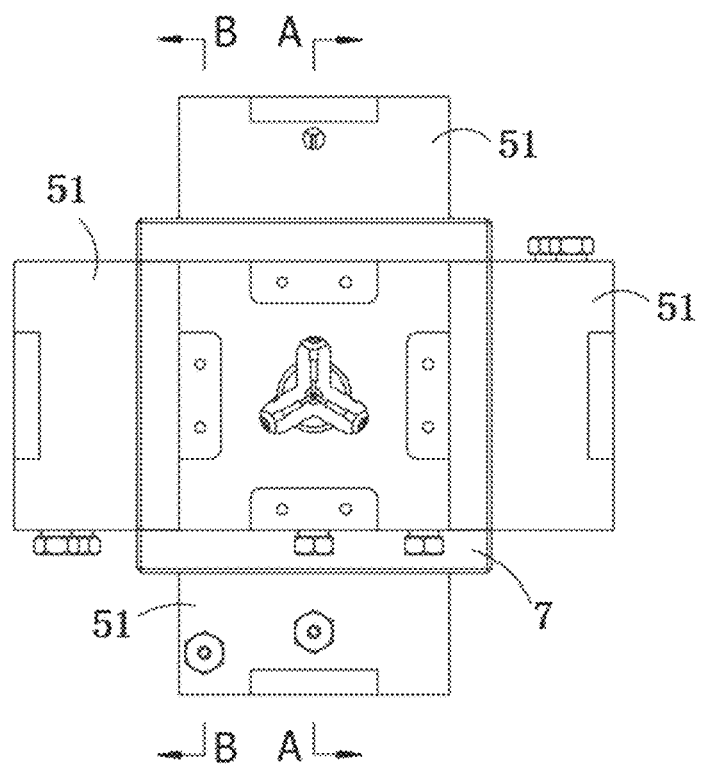
FIG. 7 is a front view of an elastic pressure box according to an embodiment.
Figure 8:
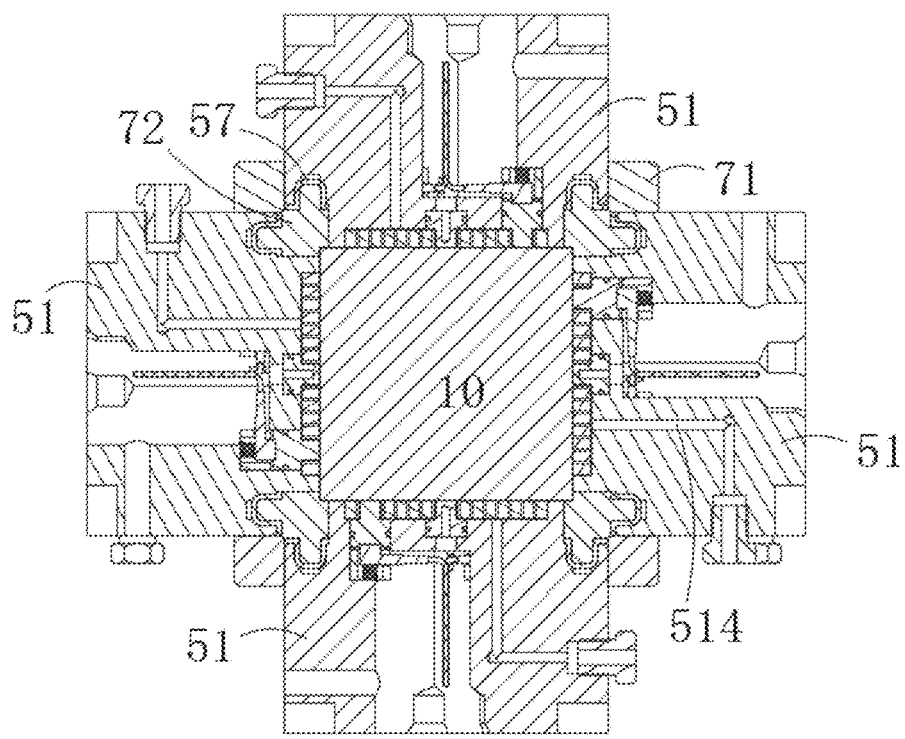
FIG. 8 is a cross-sectional view at A-A in FIG. 7.

In a possible design, as shown in FIG. 6, at least one displacement detection mechanism 6 is provided between two indenters 51 in the X-axis direction, between two indenters 51 in the Y-axis direction and between two indenters 51 in the Z-axis direction, so that the cubic sample 10 can be monitored for deformation in the X, Y and Z directions.

Optionally, the second displacement sensor 66 is an LVDT sensor.

In a possible design, the displacement detection mechanism 6 comprises a first connection arm 61, a second connection arm 62, a second displacement sensor 66 and an extensometer rod 67, the first connection arm 61 and the second connection arm 62 are respectively fixed on side parts of the two indenters 51 in the same axial direction, one end of the second displacement sensor 66 is connected to the first connection arm 61, one end of the extensometer rod 67 is connected to the second connection arm 62, and the other end of the second displacement sensor 66 is connected or in contact with the other end of the extensometer rod 67. When the cubic sample 10 is deformed, the two indenters 51 move toward each other, and the extensometer rod 67 pushes the second displacement sensor 66 to contract, so that the deformation amount of the cubic sample 10 is detected by the second displacement sensor 66.

Figure 19:
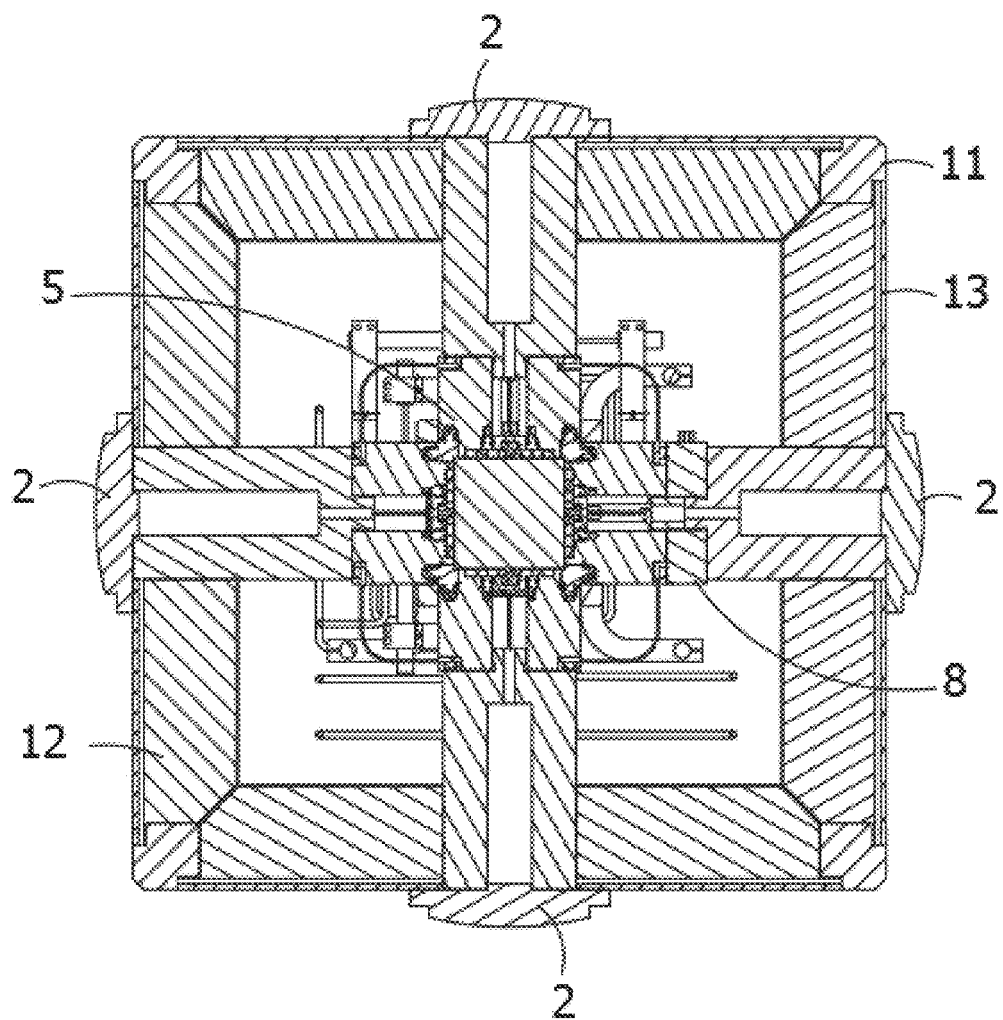
FIG. 19 is a cross-sectional view of an experimental cabin when the butting indenter is mounted with a heating plate according to an embodiment.

In a possible design, as shown in FIG. 19, an electric heating plate 8 is mounted at a front end of at least one of the butting indenters 2, and an electric heating rod is mounted in the electric heating plate 8.

Optionally, an electric heating plate 8 is provided at a front end of only one butting indenter 2, which is used to generate opposing temperature differential.

Optionally, an electric heating plate 8 is mounted at a front end of each butting indenter 2.

Figure 20:
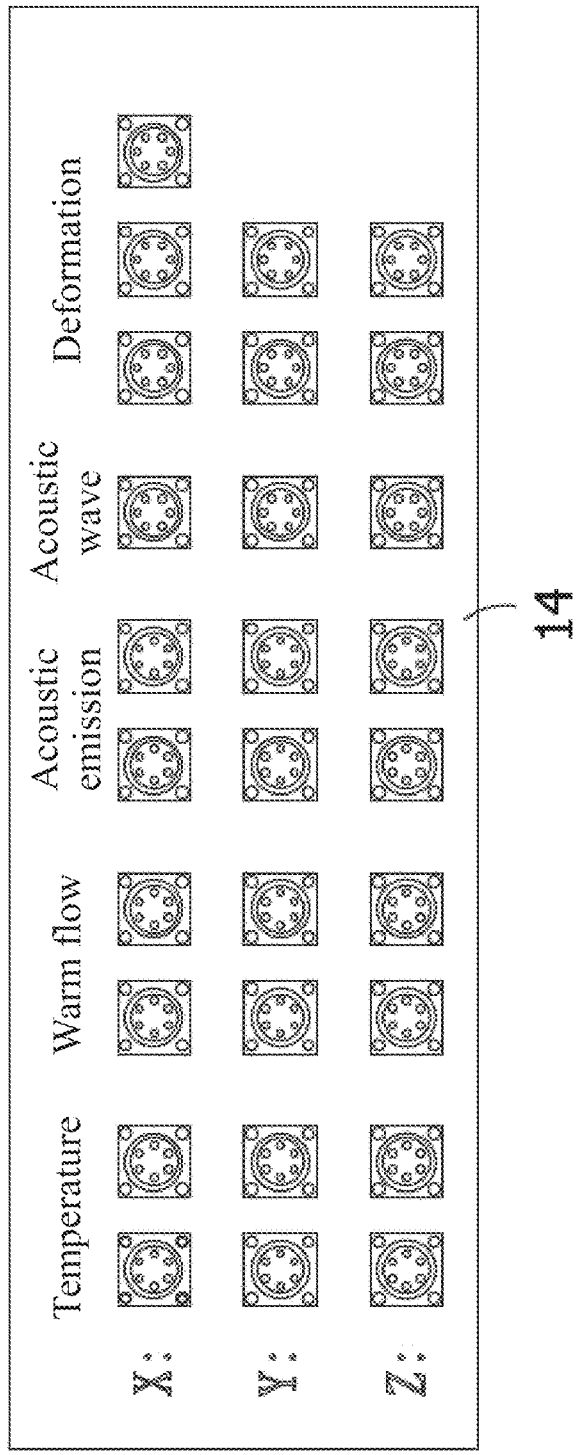
FIG. 20 is a front view of an aviation connector area according to an embodiment.

As shown in FIGS. 4 and 20, a side surface of the box body 1 is provided with an aviation connector area 14, the aviation connector area 14 is provided with a temperature aviation connector, a warm flow aviation connector, an acoustic emission aviation connector, an acoustic wave aviation connector and a deformation aviation connector that are adapted to 6 indenters 51, the temperature aviation connector is connected to a temperature sensor at the front end of the indenter 51, the warm flow aviation connector is connected to a heat flow sensor at a front end of the indenter 51, the acoustic emission aviation connector is connected to an acoustic emission probe 58, the acoustic wave aviation connector is connected to an ultrasonic probe 59, and the deformation aviation connector is connected to a displacement detection mechanism 6. The temperature aviation connector and the warm flow aviation connector are connected to a temperature monitoring system, the acoustic emission aviation connector is connected to the acoustic emission monitoring system, the acoustic wave aviation connector is connected to an acoustic wave monitoring system, and the deformation aviation connector is connected to a deformation monitoring system.

The deep rock in situ environment reconstruction and integrated three-dimensional mechanical-thermo-acousto-seismic-flow testing method according to this embodiment specifically comprises the following steps:

S1: preparing a cubic sample 10: selecting dry coal rock, and processing into a cube with a side length of 100 mm and 12 edges chamfered at 45°.

S2: placing a 100×100×100 mm cubic sample 10 within the flexible inner cubic frame 72, wherein 12 outside corner positions 723 of the flexible inner cubic frame 72 are attached to 12 inside corners of the rigid outer cubic frame 71.

S3: respectively 6 indenters 51 into the sample holder 7 to contact with six faces of the cubic sample 10, wherein the annular flanges 722 of the flexible inner cubic frame 72 in 6 directions are correspondingly mounted into the annular sealing grooves 571 of the 6 circumferential sealing strips 57;

using 12 elastic pieces 52 to connect 6 indenters 51 together, wherein a periphery of each indenter 51 is connected to 4 indenters 51 on the periphery through one elastic piece 52, the elastic piece 52 is screwed to the indenter 51, and the 6 indenters 51 can be assembled together through the 12 elastic pieces 52, so that the indenters are tightly fixed and attached to the cubic sample.

S4: placing the 6 indenters 51, the cubic sample 10 and the sample holder 7 in a box body 1, and mounting 6 butting indenters 2 to 6 faces of the box body 1, wherein the front ends of the 6 butting indenters 2 are respectively butted with rear ends of the 6 indenters 51.

Figure 21:
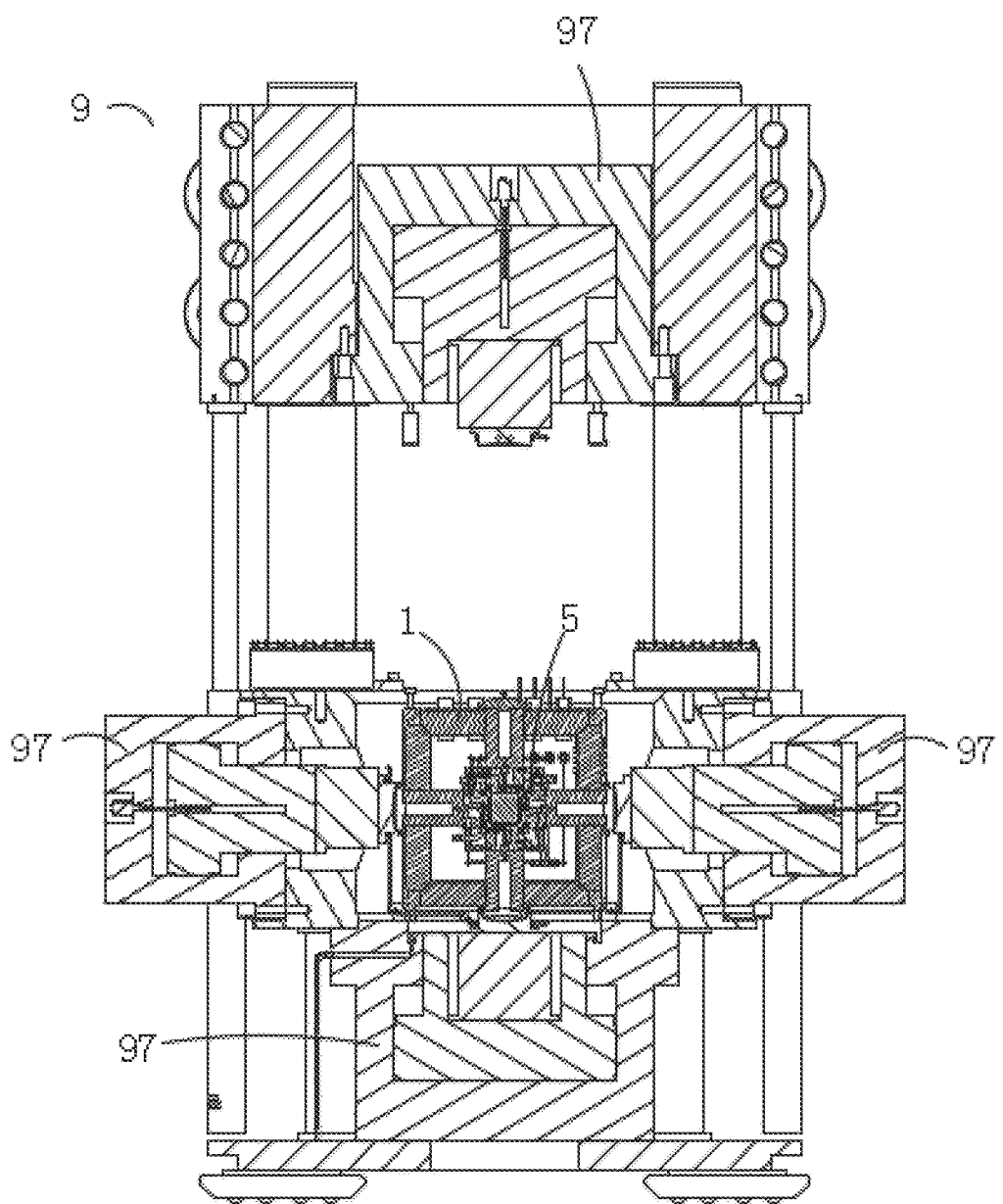
FIG. 21 is a schematic diagram of the experimental cabin placed in the loading frame beam of the three-axis six-direction loading system according to an embodiment.
Figure 22:
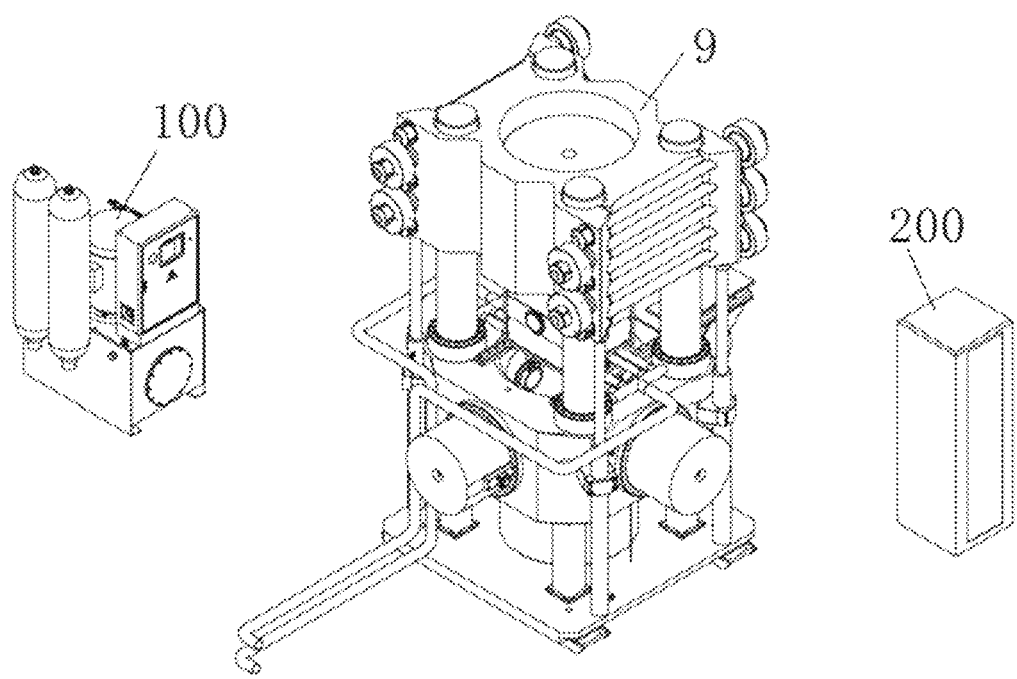
FIG. 22 is a schematic diagram of a multi-field multi-parameter integrated rock three-dimensional mechanical-thermo-acousto-seismic-flow testing system according to an embodiment.

S5: as shown in FIG. 21, placing the box body 1 on a loading frame beam 92 of a three-axis six-direction loading system 9, wherein 6 hydraulic actuators 97 of the three-axis six-direction loading system 9 are each butted with a rear end of one of the butting indenters 2;

three-way sealing: the sealing main pipe 43 is connected to a high-pressure plunger pump of an external hydraulic sealing system 100, and a sealing medium is injected into the sealing medium injection channels 515 of the 6 indenters 51 through the high-pressure plunger pump, so that a sealed high-strength rubber sleeve on the edge of the indenter is tightly fitted to the rubber frame of the cubic frame loaded with the sample, 12 edges of the cubic sample 10 are tightly attached to the flexible inner cubic frame 72, and a three-way sealing effect is achieved.

S6: vacuumizing: starting six hydraulic actuators 97 of the three-axis six-direction loading system 9, and loading the forces in three directions to 2-5% of a predetermined load value in advance; closing the stop valves on the percolation channels of 5 indenters 51, opening the stop valve on the percolation channel of the other indenter 51, connecting the percolation channel with an external vacuumizing device 200 to vacuumize the cubic sample 10 for two hours, wherein the vacuum degree reaches 1000 Pa; closing the vacuum pump of the vacuum pumping device 200 and closing the stop valve on the percolation channel.

S7: stress loading: starting a high-pressure oil pump, injecting oil and pressurizing oil to the oil cylinder of the hydraulic actuator 97 by using an independent high-pressure oil pump, and ensuring that the pressure value of the pump is higher than the pressure of percolation gas; wherein force control loading is adopted, step-by-step sequential cyclic loading is performed, and the number of the steps in the three directions is equal, so that a sample is prevented from being crushed, and the actual working condition is simulated more accurately; the up-down direction is a Z direction, the left-right direction is an X direction, the front-back direction is a Y direction, the loading sequence is Z direction→X direction→Y direction→Z direction, and the circulation is increased by 1 MPa to the predetermined load value.

S8: fluid adsorption: connecting the three percolation inlet pipes 41 with a gas cylinder, opening stop valves on the three percolation inlet pipes 41 and the three percolation outlet pipes 42, filling gas into the cubic sample 10, observing the dynamic change condition of the gas pressure, and closing the stop valves on the three percolation outlet pipes 42 after the numerical value of a flow meter is stable; adsorbing for 12 hours until the adsorption is balanced.

S9: opening a stop valve on the percolation pipe 42, observing the change rule of the pressure change of the air outlet along with the time, and waiting until the pressure of the gas at the air outlet is stable; modulating the pressure, loading mode, and gas pressure in the X, Y, and Z directions, and repeating the steps S7 to S9;

during the process, the following data are dynamically measured: XYZ three-direction pressure, fluid pressure, transverse deformation of the cubic sample 10, axial deformation of the cubic sample 10, temperature, heat flow, percolation fluid flow, acoustic data and acoustic emission data.

It should be noted that only the stop valve in a certain direction is opened each time, so that mutual influence is avoided.

S10: stopping experiment: firstly, turning off a gas cylinder, unloading the pressure of a sealed plunger pump, and finally unloading the stress, wherein the unloading sequence is Y direction→X direction→Z direction→Y direction, the circulation is gradually decreased by 1 MPa, and after the unloading is completed, turning off an oil pump corresponding to each oil cylinder;

finally, storing all data; and taking out the sample and observing the shape of the sample.

It should be noted that when the permeability in the single Z direction is measured, the percolation channels in X and Y directions are closed, and so on when the permeability in the other directions is measured.

If a high-temperature environment is required, hot air is sent into the box body 1 to heat the cubic sample 10 inside; if a low-temperature environment is required, liquid nitrogen is injected into the box body 1 through the cold source port 33 to cool the cubic sample 10 inside.

The present application can achieve three-way multi-parameter synchronous monitoring and acquisition of sample deformation, acoustic emission, ultrasonic waves, a temperature field, a percolation field, a stress strain field and a heat flow field, and has great significance for the construction of a new deep underground engineering science theory, the evaluation of deep resources, the research and development of basic theories and technologies such as exploitation and application and the like.

Embodiment 2

This embodiment discloses a fracturing testing method, which comprises the following steps:

S1: preparing a cubic sample 10: processing the coal-rock sample into a 100 mm×100 mm×100 mm standard cubic coal-rock sample; after the overall dimension of the sample is processed, drilling a crack hole with a diameter of 12 mm and a length of 100 mm in the middle of the sample along a direction vertical to a predetermined face, cleaning the crack hole by using acetone or alcohol, and waiting until the sample is dried;

S2: sample mounting and three-way sealing: this step is the same as that of Embodiment 1 and is not described here;

S3: preloading: starting an acoustic emission testing device, and loading forces in upper, lower, left, right, front and rear directions to 2-5% of a predetermined load value in advance to check whether abnormal conditions exist or not;

S4: loading: loading in a force control mode, and sequentially and circularly loading step by step, wherein the number of the steps in the three directions is equal; the up-down direction is a Z direction, the left-right direction is an X direction, the front-back direction is a Y direction, the loading sequence is Z direction→X direction→Y direction→Z direction, and the circulation is increased by 1 MPa to the predetermined load value;

S5: hydraulic fracturing: starting a plunger pump pressure adjusting device, and injecting high-pressure water into the cubic sample 10, wherein the water pressure is loaded in stages, the pressure difference of each stage is 1 MPa, the pressure is increased step by step, and the operation can be stopped when the water injection pressure suddenly drops; and S6: unloading: the unloading sequence is Y direction→X direction→Z direction→Y direction, and the circulation is decreased by 1 MPa.

In the experiment process, the acoustic emission and ultrasonic monitoring system is started, and parameters such as deformation, acoustic emission, ultrasonic waves, fluid flow, fluid pressure and the like of the cubic sample 10 in the experiment process are monitored and recorded in real time; and after the experiment is completed, all data are stored; and the sample is taken out, and the shape of the sample is observed.

The objectives, technical solutions and beneficial effects of the present application are further explained in detail with reference to the specific implementations described above, and it should be understood that the above-mentioned contents are merely specific implementations of the present invention, and are not intended to limit the protection scope of the present invention. Any modification, equivalent substitution, improvement and the like made within the spirit and principle of the present invention shall all fall within the protection scope of the present invention.

What is claimed is:

1. A deep rock in situ environment reconstruction and integrated three-dimensional mechanical-thermo-acousto-seismic-flow testing method, comprising the following steps:

S1: preparing a cubic sample;

S2: placing the cubic sample in a sample holder, wherein the sample holder is provided with ports that are adapted to indenters in upper, lower, left, right, front and rear directions;

S3: respectively extending front ends of the 6 indenters into the sample holder from the ports of the sample holder in 6 directions to contact with six faces of the cubic sample;

wherein the front end of each indenter is provided with a plurality of permeation holes, each indenter is provided with a seepage medium channel, and one end of the percolation medium channel is communicated with the plurality of permeation holes; the front end of the indenter is provided with a temperature sensor, a heat flow sensor, an acoustic emission probe and an ultrasonic probe;

S4: placing the 6 indenters, the cubic sample and the sample holder in a box body, and mounting 6 butting indenters to 6 faces of the box body, wherein the butting indenters can move axially relative to the box body, and front ends of the 6 butting indenters are respectively butted with rear ends of the 6 indenters;

S5: placing the box body on a loading frame beam of a three-axis six-direction loading system, wherein 6 hydraulic actuators of the three-axis six-direction loading system are each butted with a rear end of one of the butting indenters;

S6: making inner edges of the ports of the sample holder in 6 directions in sealing contact with the cubic sample;

S7: comprising:

stress loading: performing stress loading on the cubic sample by using a hydraulic actuator;

filling a fluid medium into the cubic sample through the percolation medium channel;

wherein the following data are dynamically measured: fluid pressure, deformation of the cubic sample, percolation fluid flow, acoustic wave data and acoustic emission data.

2. The deep rock in situ environment reconstruction and integrated three-dimensional mechanical-thermo-acousto-seismic-flow testing method according to claim 1, wherein the box body is provided with an air inlet, an air outlet and a cold source port;

if a high-temperature environment is required during the experiment, hot air is sent into the box body through the air inlet; and if a low-temperature environment is required, liquid nitrogen is injected into the box body through the cold source port.

3. The deep rock in situ environment reconstruction and integrated three-dimensional mechanical-thermo-acousto-seismic-flow testing method according to claim 1, wherein the sample holder comprises a rigid outer cubic frame and a flexible inner cubic frame, the rigid outer cubic frame and the flexible inner cubic frame are both provided with 12 frame edges, 6 faces of the rigid outer cubic frame and 6 faces of the flexible inner cubic frame are both rectangular frames, 12 outside corner positions of the flexible inner cubic frame are attached to 12 inside corners of the rigid outer cubic frame, and the cubic sample is loaded in the flexible inner cubic frame; and in the S6, inner edges of rectangular openings of the flexible inner cubic frame in 6 directions are in sealing contact with the cubic sample.

4. The deep rock in situ environment reconstruction and integrated three-dimensional mechanical-thermo-acousto-seismic-flow testing method according to claim 3, wherein the front end of the indenter is provided with an annular groove, a circumferential sealing strip is embedded in the annular groove, a sealing medium injection channel is provided in the indenter, one end of the sealing medium injection channel is communicated with the annular groove, and the other end of the sealing medium injection channel is connected to a hydraulic sealing system;

each face of the flexible inner cubic frame is provided with an integrally-manufactured annular flange, and the annular flange is adapted to an annular sealing groove of the circumferential sealing strip;

in the S3, when the front ends of 6 indenters respectively extend into the sample holder from the ports of the sample holder in 6 directions to contact with six faces of the cubic sample, the annular flanges are correspondingly mounted in the annular sealing grooves of the circumferential sealing strips on the 6 indenters; and in the S6, the percolation medium channels of all the indenters are closed, and a sealing medium is injected into the sealing medium injection channels of the 6 indenters through the hydraulic sealing system, so that 12 edges of the cubic sample are tightly attached to the flexible inner cubic frame, and a three-way sealing is achieved.

5. The deep rock in situ environment reconstruction and integrated three-dimensional mechanical-thermo-acousto-seismic-flow testing method according to claim 3, wherein the indenter comprises an indenter body and a permeation block, a front end of the indenter body is provided with an annular groove and a rectangular convex block, the annular groove is located at an edge of the front end of the indenter body, and the rectangular convex block is located on an inner periphery of the annular groove;

a front end face of the rectangular convex block is provided with an integrally-manufactured embedding groove, the permeation block is embedded in the embedding groove, a plurality of permeation holes are provided on the permeation block, and the permeation holes are communicated with the permeation block from front to back; and a percolation medium channel and a sealing medium injection channel are provided in the indenter body, one end of the percolation medium channel is communicated with the embedding groove, and the other end of the sealing medium injection channel and the percolation medium channel is communicated with an outer surface of the indenter body.

6. The deep rock in situ environment reconstruction and integrated three-dimensional mechanical-thermo-acousto-seismic-flow testing method according to claim 1, wherein a displacement detection mechanism is provided between the two indenters in the same axial direction, and the deformation of the cubic sample is monitored by the displacement detection mechanism.

7. The deep rock in situ environment reconstruction and integrated three-dimensional mechanical-thermo-acousto-seismic-flow testing method according to claim 1, wherein the hydraulic actuator comprises a cylinder barrel, a piston and an actuating indenter, the actuating indenter is connected to a free end of the piston, and the actuating indenters of the 6 hydraulic actuators are each configured to adapt to the rear end of one of the butting indenters; and a first displacement sensor is arranged between the cylinder barrel and the piston, and a force sensor is arranged between the actuating indenter and the piston.

8. The deep rock in situ environment reconstruction and integrated three-dimensional mechanical-thermo-acousto-seismic-flow testing method according to claim 1, wherein in the S3, after 6 indenters are butted with the sample holder, 12 elastic pieces are used to connect the 6 indenters together, so that the cubic sample, the sample holder and the 6 indenters form a whole, and a periphery of each indenter is connected to 4 indenters on the periphery through one elastic piece.

9. The deep rock in situ environment reconstruction and integrated three-dimensional mechanical-thermo-acousto-seismic-flow testing method according to claim 1, wherein the S1 specifically comprises: processing a coal-rock sample into a 100 mm×100 mm×100 mm standard cubic coal-rock sample; after an overall dimension of the sample is processed, drilling a crack hole with a diameter of 12 mm and a length of 100 mm in a middle of the sample along a direction vertical to a predetermined face, cleaning the crack hole by using acetone or alcohol, and waiting until the sample is dried;
the S7 comprises:
preloading: starting an acoustic emission monitoring system, and loading forces in upper, lower, left, right, front and rear directions to 2-5% of a predetermined load value in advance to check whether abnormal conditions exist or not;
loading: loading in a force control mode, and sequentially and circularly loading to a predetermined load value step by step; and
hydraulic fracturing: injecting high-pressure water into the cubic sample, wherein the water pressure is loaded in stages.

10. The deep rock in situ environment reconstruction and integrated three-dimensional mechanical-thermo-acousto-seismic-flow testing method according to claim 1, wherein in the S6, after the sample holder is in sealing contact with the cubic sample, the percolation medium channels of 5 indenters are closed, the percolation medium channel of the other indenter is opened, the percolation medium channel is connected to an external vacuumizing device for vacuumizing, and the vacuumizing device and the percolation medium channels are closed after a period of time;
in the S7, fluid adsorption is performed after stress loading:
opening the percolation medium channels of the indenters, wherein the percolation medium channels of one of the indenters in the X-axis direction, one of the indenters in the Y-axis direction and one of the indenters in the Z-axis direction is used as three percolation fluid injection channels, and the percolation medium channels of the other indenter in the X-axis direction, the other indenter in the Y-axis direction and the other indenter in the Z-axis direction are used as three percolation fluid outflow channels; percolation fluid is filled into the percolation fluid injection channels, and after a flow rate is stable, the percolation fluid outflow channels are closed;
after the adsorption is balanced, opening the percolation fluid outflow channel, observing a change rule of the pressure at an outlet of the percolation fluid outflow channel along with time, and waiting until the pressure of the fluid at the outlet of the percolation fluid outflow channel is stable;
during the process, dynamically measuring the following data: XYZ three-direction pressure, fluid pressure, deformation of the cubic sample, temperature, heat flow, percolation fluid flow, acoustic data and acoustic emission data; and
when a permeability in a single axial direction is measured, opening the percolation medium channels of two indenters in the single axial direction, and closing the percolation medium channels in the other two axial directions.

\* \* \* \* \*